United States Patent [19]

Labeeuw et al.

[11] Patent Number: 4,578,377

[45] Date of Patent: Mar. 25, 1986

[54] DERIVATIVES OF CEPHALOSPORINS, THEIR PROCESS OF SEPARATION AND ANTIBIOTIC DRUGS CONTAINING THE SAID DERIVATIVES

[75] Inventors: Bernard Labeeuw, Montpellier; Ali Salhi, Saint-Gely-Du-Fesc, both of France

[73] Assignee: Sanofi, Paris, France

[21] Appl. No.: 723,709

[22] Filed: Apr. 16, 1985

Related U.S. Application Data

[63] Continuation of Ser. No. 513,008, Jul. 12, 1983, abandoned.

[30] Foreign Application Priority Data

Jul. 13, 1982 [FR] France ............................... 82 12317

[51] Int. Cl.$^4$ .................. A61K 31/545; C07D 501/34
[52] U.S. Cl. ..................................... 514/206; 544/27
[58] Field of Search ........................... 544/27; 514/206

[56] References Cited

U.S. PATENT DOCUMENTS 3,278,531 10/1966 Cox et al. ............................ 424/246
4,399,131 8/1983 Durekheimer et al. .............. 544/22

Primary Examiner—Donald G. Daus
Assistant Examiner—Mary E. Ceperley
Attorney, Agent, or Firm—Stevens, Davis, Miller & Mosher

[57] ABSTRACT

The present invention relates to cephalosporins having the formula:

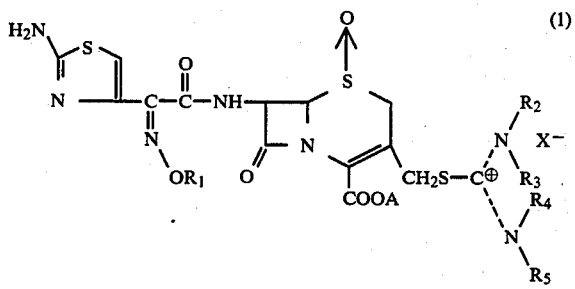

in which COOA is an acidic radical, salt or ester, and $R_1$ represents a group:

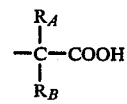

in which $R_A$ and $R_B$ are H or alkyl or together form a cycloalkyl with the carbon to which they are bonded, $R_2$ and $R_3$ are H, alkyl or alkenyl, $R_4$ and $R_5$ are H, alkyl or alkenyl or together form a ring to the nitrogen atom with which they are bonded. This invention also relates to a process for the preparation of these compounds and to drugs containing them.

8 Claims, No Drawings

DERIVATIVES OF CEPHALOSPORINS, THEIR PROCESS OF SEPARATION AND ANTIBIOTIC DRUGS CONTAINING THE SAID DERIVATIVES

This application is a continuation of application Ser. No. 513,008, filed July 12, 1983, now abandoned.

This invention relates to the derivatives of the family of cephalosporins, their process of preparation, and their therapeutic use.

The compounds of the invention have the formula:

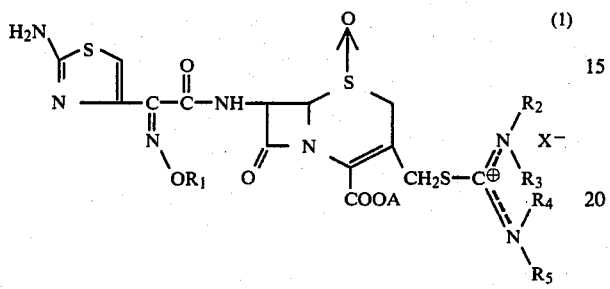

in which:
the

group in position 4 is an acidic radical or an alkaline or alkaline-earth metal salt, or an amine salt, such as triethylamine or an ester radical that is easily hydrolysable or metabolically labile and pharmaceutically acceptable, $R_1$ represents a group:

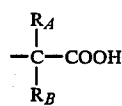

in which $R_A$ and $R_B$ each independently designates hydrogen, or a lower alkyl group, preferably a methyl group, or $R_A$ and $R_B$ taken together form a cycloalkyl, preferably cyclobutyl, with the carbon atom to which they are bonded, $R_2$ and $R_3$ each independently designates hydrogen, a lower alkyl group or a lower alkenyl group: the designation lower alkyl refers to an alkyl containing 1 to 4 carbon atoms; the designation lower alkenyl refers to an alkenyl containing 2 to 4 carbon atoms, $R_4$ and $R_5$ each independently designates hydrogen, a lower alkyl group, a lower alkenyl group, or $R_4$ and $R_5$ taken together with the nitrogen atom to which they are bonded form a ring with 5 or 6 links possibly containing a second nitrogen atom, and particularly the following rings:

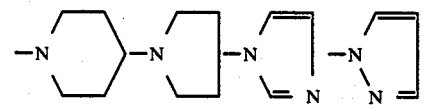

$X^-$ designates the anion of the acid in which in compound (1) is in the form of betaine.

The double bond of the isothiouronium function may be delocalized as shown in the formula of the compound (1).

Due to the presence of an oxime group in the formula, the compounds (1) exist in two isomeric forms, syn and anti. The syn isomeric, which display greater therapeutic activity, are the preferred compounds.

It is understood that the compounds (1) indicated above may exist:
either in the form indicated in formula (1)
or in the tautomer form (1'):

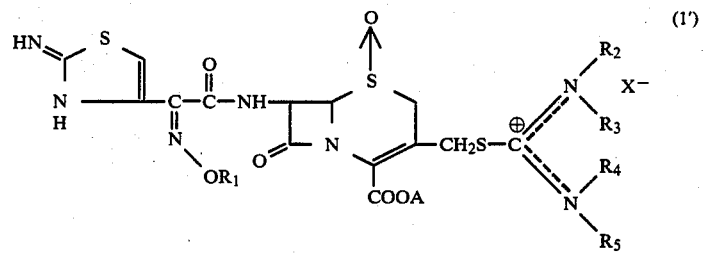

in which A, $R_1$, $R_2$, $R_3$, $R_4$ and $R_5$ have the meanings indicated above.

The invention also relates to a process for the preparation of compounds of formula (1).

This process consists of first aliphatising amino-7 bromomethyl-3 cephem-3 carboxylate of tertiobutyl-4 S-oxide (2) by acid (3) according to the reaction scheme below in which $R'_1$ represents the t-butyl ester corresponding to $R_1$:

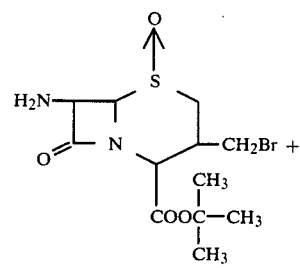
(2)

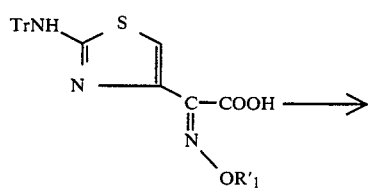
(3)

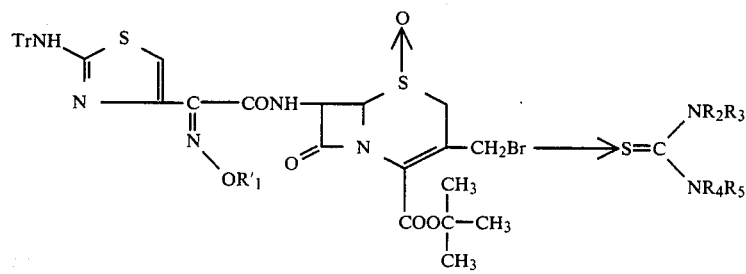
(4)

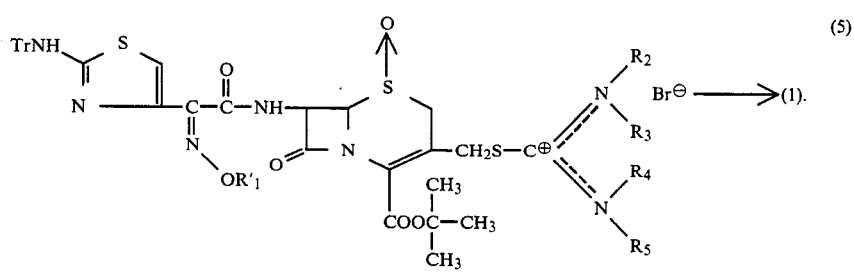
(5)

(Tr = trityl)

Before performing the aliphatisation reaction, it is advisable to replace the amino group of the acid by a protecting group easy to eliminate subsequently. It is possible to use the groups normally employed in organic synthesis for the protection of amino groups, and in particular the trityl group.

Similarly, if the substituent $R_1$ of the acid (3) has a carboxyl group, it is necessary to convert the latter to an ester. The ester selected is preferably sufficiently labile to be able to regenerate the acidic function at the end of the reaction. Tertiobutyl ester is normally used.

To perform the aliphatisation reaction, it is necessary to proceed with the activation of the carboxyl group of compound (3), preferably by conversion to the anhydride using a carbodiimide, generally dicyclohexylcarbodiimide.

The activation reaction is performed in a suitable organic solvent such as tetrahydrofuran at a temperature between 0° and 50° C., and preferably at ambient temperature. The activation reaction may be facilitated by the addition of a hydroxylated derivative such as hydroxy-1 benzotriazole.

The solution of the aliphatisation reagent thus obtained, rid of the dicyclohexylurea formed by filtration, is added to a solution of compound (2) in a solvent such as dimethylformamide. The two reagents can also be added in the reverse order.

Aliphatisation can also be performed by the acid chloride of (3):

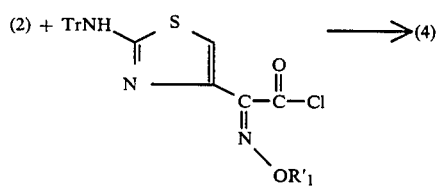

Thiourea is added to compound (4) thus obtained:

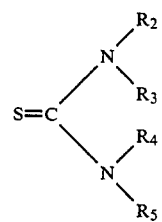

where $R_2$, $R_3$, $R_4$ and $R_5$ have the values designated above.

The reaction is carried out in a suitable solvent such as dimethylformamide or N,N-dimethylacetamide in the presence of a base such as triethylamine.

To obtain compound (1), the protecting group on the amine and the tertiobutyl ester group or groups are eliminated by a known process, especially by hydrolysis in acidic medium, using an organic acid such as formic acid or trifluoracetic acid, or a mixture of hydrochloric and acetic acids.

As for the raw materials for the reaction, compounds (2) and compound (3) and its derivatives in which the amino group is blocked by a protecting group are known.

Preparation of thioureas:

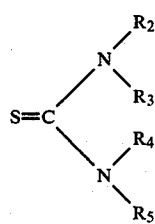

The thioureas in which $R_2$, $R_3$, $R_4$ and $R_5$ represent alkyl or alkenyl groups are prepared by the methods described in E. H. Rodd, Chemistry of Aliphatic Compounds, Vol. 1B, Elsevier 1952, pp.924–929.

The thioureas in which $R_4$ and $R_5$ taken together with the nitrogen atom to which they are bonded form a ring with 5 or 6 links, are prepared from dimethylthiocarbamoyl chloride or methyl isothiocyanate, with which the nitrogenated heterocycle is caused to react according to the reaction scheme below:

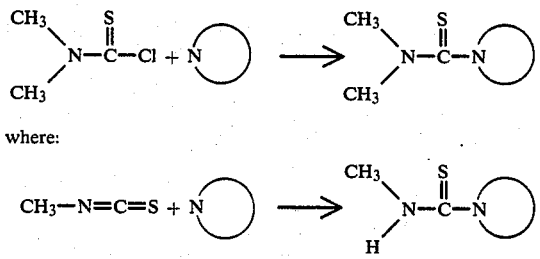

where:

The compounds (1) of the invention in which A is different from H are obtained from compounds (1) in which A is H by reactions which are themselves known.

Hence the inorganic salts are obtained by action on compounds (1) in which A is H of an inorganic base such as caustic soda or caustic potash or sodium bicarbonate in equimolecular quantities. The salification reaction is performed in a solvent such as water or ethanol, and the salt obtained is isolated by evaporation of the solution.

The salts of organic bases are obtained by the action, on a solution of the acid (1) (A=H) in a solvent or a mixture of suitable solvents, of an equimolecular quantity of the organic base. The salt is isolated by precipitation with ether.

The esters are obtained by known esterification processes. For example, effective use can be made of the action of a halogenated derivative on a salt such as the sodium salt of the acid. The reaction is performed preferably in a solvent capable of dissolving the starting acidic derivative, as in dimethylformamide.

The syn and anti isomers are obtained by a suitable choice of reagents or experimental conditions.

The following examples offer a better understanding of the scope of the invention.

As normally encountered in this family of compounds, the products according to the invention do not exhibit a sharp melting point, but only decomposition points not allowing them to be characterized by melting point.

The products are therefore characterized by their nuclear magnetic resonance spectrum recorded at 60 MHz or at 250 MHz, using hexamethyldisiloxane as the internal standard.

The spectra are recorded in deuteriated dimethylsulfoxide.

The following abbreviations will be used:
S singlet
D doublet
D of D doublet of doublet
Se. enlarged singlet
M multiplet
Q quadruplet
AB system AB
J represents the coupling constant.

In addition, elementary microanalyses were performed in each case and agree with the formulas indicated.

EXAMPLE 1

Trifluoracetate of ((amino-2 thiazolyl-4)-2 (carboxy-2 propyl-2 oxyimino)-2 acetamido)-7 (N,N,N',N'-tetramethyl uronium thiomethyl)-3 cepheme-3 carboxyl-4 S-oxide-1 acid, syn isomer (1) $R_1 = -C(CH_3)_2CO_2H$  $R_2=R_3=R_4=R_5=CH_3$
$X=CF_3CO_2^-$
CM 41 089

(a) ((tritylamino-2 thiazolyl-4)-2 (t.butoxycarbonyl-2 propyl-2 oxyimino)-2 acetamido)-7 bromethyl-3 cepheme-3 carboxylate of t-butyl-4 S-oxide-1, syn isomer

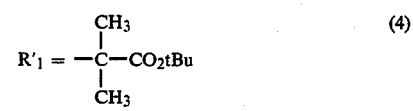

To 830 mg of amino-7 bromethyl-3 cepheme-3 carboxylate-4 hydrochloride of t-butyl S-oxide-1 dissolved in 15 ml methylene chloride, are added 209 mg of tritylamino-2 thiazolyl-4)-2 (terbutoxy carbonyl-2 propyl-2 oxyimino)-2 acetic acid, 422 mg dicyclohexylcarbodiimide and 10 mg hydroxy-1 benzotriazole.

After four hours agitation at ambient temperature, the dicyclohexylurea is filtered, the methylene chloride evaporated under vacuum, the residue dissolved in ether, washed with a normal hydrochloric acid solution and then with water, followed by a saturated solution of sodium bicarbonate and then water. The ether phase is dried over magnesium sulfate and then concentrated under vacuum. It is chromatographed on 80 g silica gel and eluted with the 60:40 (v/v) hexane/ethyl acetate mixture. The eluate is evaporated to obtain 650 mg of (a).

DIFFERENT PREPARATION OF (A)

A suspension of 20 g of (tritylamino-2 thiazolyl-4)-2 (t-butoxy carbonyl-2 propyl-2 oxyimino)-2 acetic acid is prepared in 100 ml methylene chloride cooled to 0° to 2° C. 7.3 g PCl$_5$ are slowly added and the mixture agitated for 30 minutes at this temperature. Precipitation is obtained by adding one liter of hexane, followed by filtration and drying under vacuum to obtain 21.2 g (tritylamino-2 thiazolyl-4)-2 (t-butoxycarbonyl-2 propyl-2 oxyimino)-2 acetic acid.

Melting point 135° C.

NMR SPECTRUM IN DEUTEROCHLOROFORM 15H at 7.40 ppm (H of trityl, S), 1H at 6.42 ppm (H of thiazole, S), 6H at 1.67 ppm (C(CH$_3$)$_2$, S), 9H at 1.45 ppm (C(CH$_3$)$_3$, S).

To a suspension of 1.5 g amino-7 bromomethyl-3 cepheme-3 carboxylate of t-butyl-4 S-oxide hydrochloride in 30 ml anhydrous methylene chloride, 2.2 g of acidic chloride previously prepared are added at 5° C., together with 1 ml N,N-dimethylaniline. The mixture is allowed to return to ambient temperature. After 2½ hours of agitation at ambient temperature, it is poured on 100 ml isopropyl ether for precipitation, filtration, washing with isopropyl ether and then with hexane, and drying under vacuum to obtain 3 g of (a).

(b) Bromide of ((tritylamino-2 thiazolyl-4)-2 (t-butoxy carbonyl-2 propyl-2 oxyimino)-2 acetamido)-7, N,N,N',N'-tetramethyl uronium thiomethyl-3 cephem-3 carboxylate of t-butyl-4 S-oxide-1, syn isomer A solution of 1 g of (a) and 0.21 g N,N'-tetramethyl thiourea in 5 ml N,N-dimethylacetamide are left to stand for two days at 5° C. The solution obtained is poured drop by drop over 100 ml isoproyl ether with agitation.

The solid obtained is redissolved in 5 ml methylene chloride and then chromatographed on 25 g silica gel. The eluant is a 90:10 (v/v) mixture of methylene chloride and methanol. 0.7 g of product (b) is obtained.

(c) CM 41 089

A solution of 0.62 g of (b) in 4 ml trifluoracetic acid is left to stand at ambient temperature for 45 minutes. It is concentrated under vacuum and then precipitated by the addition of ether, filtered and then washed with ether and dried over phosphorus pentoxide to obtain 0.48 g of CM 41 089.

NMR SPECTRUM 1H at 8.5 ppm (CONH, D, J=9 Hz), 1H at 6.85 ppm (H of thiazole, S), 1H at 5.95 ppm (H$_7$, D of D, J=9 Hz, J=4 Hz), 1H at 5.02 ppm (H$_6$, D, J=4 Hz), 1H at 4.10 ppm (CH$_2$S, AB, J$_{AB}$=13 Hz), 1H at 3.90 ppm (CH$_2$S, AB, J$_{AB}$=13 Hz), 1H at 3.80 ppm (CH$_2$SO, AB, J$_{AB}$=17 Hz), 1H at 3.70 ppm (CH$_2$SO, AB, J$_{AB}$=17 Hz), 12H at 3.20 ppm (2(CH$_3$)$_2$N, S), 6H at 1.45 ppm ((CH$_3$)$_2$C, S).

EXAMPLE 2

Trifluoracetate of ((amino-2 thiazolyl-4)-2 carboxy-2 ethyl-2 oxyimino)-2 acetamidol)-7 (N,N,N',N'-tetramethyluronium thiomethyl)-3 cepheme-3 carboxyl-4 S-oxide-1 acid, syn isomer

SR 41 361 A

This product is prepared in the same way and in the same operating conditions as CM 41 089, starting with (tritylamino-2 thiazolyl-4)-2 (t-butoxycarbonyl-1 ethyl-1 oxyimino)-2 acetic acid.

The SR 41 361 A, a mixture of two diastereoisomers, is identified by its spectrum.

NMR SPECTRUM 1H at 8.80 ppm (CONH, 2S, J=9 Hz), 2H at 7.40 ppm (NH$_2$ of thiazole, Se.), 1H at 6.80 ppm (H of thiazole) 2S), 1H at 5.96 ppm (H$_7$, M), 1H at 5.00 ppm (H$_6$, M), 1H at 4.20 ppm

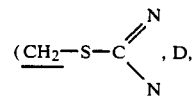

J=13 Hz), 1H at 4.55 ppm (CHCH$_3$, M), 1H at 3.85 ppm

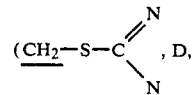

J=13 Hz), 2H at 3.75 ppm (CH$_2$—SO, M), 12H at 3.15 ppm (CH$_3$)$_2$N, Se.), 3H at 1.40 ppm (CH$_3$—CH, D, J=7 Hz).

EXAMPLE 3

Trifluoracetate of ((amino-2 thiazolyl-4)-2 carboxy-2 propyl-2 oxyimino)-2 acetamido)-7 (N-methyl, N',N'-pentamethylene uronium thiomethyl)-3 cepheme-3 carboxyl-4 S-oxide-1 acid, syn isomer

SR 41 381 A

This product is obtained by the method described above, starting with compound (a) of Example 1 and N-methyl, N',N'-pentamethylene thiourea prepared as follows.

To 2.7 ml piperidine cooled to −30°C., 2 g methyl isothiocyanate are slowly added. The mixture is diluted with 10 ml methylene chloride, agitated for one hour and evaporated to dryness under vacuum. The residue is triturated with ether and filtered. After drying, 4 g of N-methyl, N',N'-pentamethylene thiourea are obtained. Melting point 130° C.

SR 41 381 A is identified by its NMR spectrum.

1H at 9.50 ppm (NH, CH$_3$, Se.), 1H at 8.47 ppm (CONH, D, J=9 Hz), 2H at 7.50 ppm (NH$_2$, Se.), 1H at 6.90 ppm (H of thiazole, S), 1H at 5.96 ppm (H$_7$, D of D, J$_1$=9 Hz, J$_2$-4 Hz), 1H at 5.0 ppm (H$_6$, D, J=4 Hz), 2H at 4.0 ppm

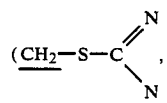

AB J$_{AB}$=13 Hz), 2H at 3.80 ppm (CH$_2$—SO, AB, J$_{AB}$=17 Hz), 4H at 3.60 ppm (CH$_2$—CH$_2$—N, Se.), 3H at 3.0 ppm (CH$_3$N, S), 6H at 1.55 ppm (—CH$_2$—CH$_2$—CH$_2$, Se.), 6H at 1.45 ppm ((CH$_3$)$_2$—C, S).

EXAMPLES 4 TO 13

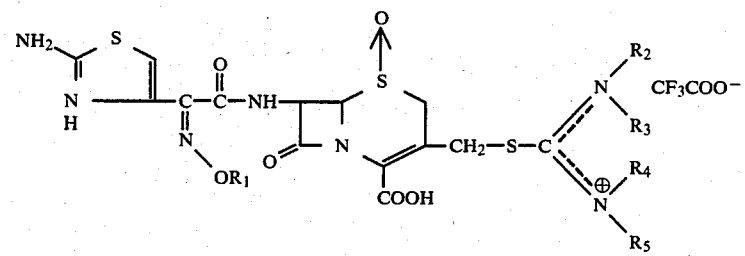

(1) Syn isomer
The significances of $R_1$, $R_2$, $R_3$ and $$-N\begin{matrix}R_4\\R_5\end{matrix}$$

are given in Table 1.

TABLE 1

| Code number | $R_1$ | $R_2$ | $R_3$ | $-N\begin{matrix}R_4\\R_5\end{matrix}$ |
|---|---|---|---|---|
| SR 41362 A | HO$_2$C— | —CH$_3$ | —CH$_3$ | —N(CH$_3$)$_2$ |
| SR 41363 A | CH$_3$—C(CH$_3$)(CO$_2$H)— | H | H | —NH$_2$ |
| SR 41380 A | CH$_3$—C(CH$_3$)(CO$_2$H)— | —CH$_3$ | —CH$_3$ | —NH—CH$_2$—CH=CH$_2$ |
| SR 41382 A | CH$_3$—C(CH$_3$)(CO$_2$H)— | —CH$_3$ | —CH$_3$ | piperidino |
| SR 41383 A | CH$_3$—C(CH$_3$)(CO$_2$H)— | —H | —CH$_3$ | —NH—CH$_3$ |
| SR 41384 A | CH$_3$—C(CH$_3$)(CO$_2$H)— | —CH$_3$ | —CH$_3$ | —NH—CH$_3$ |
| SR 41385 A | CH$_3$—C(CH$_3$)(CO$_2$H)— | C$_2$H$_5$ | C$_2$H$_5$ | —NH—C$_2$H$_5$ |
| SR 41605 A | CH$_3$—C(CH$_3$)(COOH)— | —CH$_3$ | —CH$_3$ | —NH—C$_2$H$_5$ |
| SR 41609 A | CH$_3$—C(CH$_3$)(COOH)— | H | —CH$_3$ | pyrrolidino |

TABLE 1-continued

| Code number | $R_1$ | $R_2$ | $R_3$ | $-N\begin{matrix}R_4\\R_5\end{matrix}$ |
|---|---|---|---|---|
| SR 41912 A | HO$_2$C—cyclobutyl | —CH$_3$ | —CH$_3$ | —NH—CH$_3$ |

NMR SPECTRA OF EXAMPLES 4 TO 13

| Code number | NMR spectrum |
|---|---|
| SR 41362 A | 1 H at 8.80 ppm (CON<u>H</u>, D, J: 9 Hz) - <br> 2 H at 7.50 ppm (N<u>H</u>$_2$ of thiazole, Se.) - <br> 1 H at 6.80 ppm (H thiazole, S) <br> 1 H at 5.96 ppm (H$_7$, D of D, J$_1$ = 9 Hz, J$_2$ = 4 Hz) - <br> 1 H at 5.0 ppm (H$_6$, D, J = 4 Hz) - <br> 1 H at 4.10 ppm (C<u>H</u>$_2$—S—C(N)(N), D, J = 13 Hz) - <br> 1 H at 3.90 ppm (C<u>H</u>$_2$—S—C(N)(N), D, J = 13 Hz) - <br> 2 H at 3.80 ppm (C<u>H</u>$_2$SO, AB, J$_{AB}$ = 17 Hz) - <br> 12 H at 3.10 ppm (—C—(N(C<u>H</u>$_3$)$_2$)$_2$, Se.) - <br> 4 H at 2.40 ppm (cyclobutyl-CO$_2$H, M at α of cyclobutyl) <br> 2 H at 1.85 ppm (cyclobutyl CO$_2$H, M at β of cyclobutyl) |
| SR 41363 A | 4 H at 9.40 ppm (C(N<u>H</u>$_2$)(N<u>H</u>$_2$), Se.) <br> 1 H at 8.40 ppm (CON<u>H</u>, D, J = 9 Hz) - <br> 2 H at 7.40 ppm (N<u>H</u>$_2$ of thiazole, Se.) - <br> 1 H at 6.90 ppm (H of thiazole, S) - <br> 1 H at 6.0 ppm (H$_7$, D of D, J$_1$ = 9 Hz, J$_2$ = 4 Hz) - <br> 1 H at 5.0 ppm (H$_6$, D, J = 4 Hz) - |

-continued

| Code number | NMR spectrum |
|---|---|
| | 2 H at 4.10 ppm (C$\underline{H_2}$—S—C(=N)N, AB, $J_{AB}$ = 13 Hz) |
| SR 41363 A | 2 H at 3.80 ppm (C$\underline{H_2}$—SO, AB, $J_{AB}$ = 17 Hz) - |
| | 6 H at 1.45 ppm (C(C$\underline{H_3}$)$_2$, S) |
| SR 41380 A | 1 H at 9.50 ppm (N$\underline{H}$, Se.) - |
| | 1 H at 8.50 ppm (NON$\underline{H}$, D, J = 9 Hz) - |
| | 2 H at 7.50 ppm (N$\underline{H_2}$ of thiazole, Se.) - |
| | 1 H at 6.90 ppm (H of thiazole, S) - |
| | 1 H at 5.96 ppm (H$_7$, D of , J$_1$ = 9 Hz, J$_2$ = 4 Hz) - |
| | 1 H at 5.80 ppm (—CH$_2$—C$\underline{H}$=CH$_2$, M) - |
| | 2 H at 5.10 ppm (—CH$_2$—CH=C$\underline{H_2}$, M) - |
| | 1 H at 5 ppm (H$_6$, D, J = 4 Hz) - |
| | 3 H at 4.10 ppm (C$\underline{H_2}$—S and C$\underline{H_2}$—N, M) - |
| | 1 H at 3.95 ppm (C$\underline{H_2}$—S, D, J = 13 Hz) - |
| | 2 H at 3.90 ppm (C$\underline{H_2}$—SO, AB, J = 17 Hz) - |
| | 6 H at 3.20 ppm ((C$\underline{H_3}$)$_2$N, S) - |
| | 6 H at 1.45 ppm ((C$\underline{H_3}$)$_2$C—CO$_2$H, S) |
| SR 41382 A | 1 H at 8.47 ppm (N$\underline{H}$CO, D, J = 9 Hz) - |
| | 2 H at 7.40 ppm (N$\underline{H_2}$ of thiazole, Se.) - |
| | 1 H at 6.90 ppm (H of thiazole, S) - |
| | 1 H at 5.95 ppm (H$_7$, D of D, J$_1$ = 9 Hz, J$_2$ = 4 Hz) |
| | 1 H at 5.6 ppm (H$_6$, D, J = 4 Hz) - |
| | 2 H at 4.0 ppm (C$\underline{H_2}$—S—C(=N)N, AB, $J_{AB}$ = 13 Hz) - |
| | 2 H at 3.80 ppm (C$\underline{H_2}$SO, AB, $J_{AB}$ = 17 Hz) - |
| | 4 H at 3.55 ppm (C$\underline{H_2}$N, Se.) - |
| | 6 H at 3.10 ppm ((C$\underline{H_3}$)$_2$N, S) - |
| | 6 H at 1.55 ppm (C$\underline{H_2}$—CH$_2$CH$_2$, SE.) - |
| | 6 H at 1.45 ppm (C(C$\underline{H_3}$)$_2$, S) |
| SR 41383 A | 1 H at 9.50 ppm (N$\underline{H}$CH$_3$, Se.) - |
| | 1 H at 9.40 ppm (N$\underline{H}$CH$_3$ Se.) - |
| | 1 H at 8.47 ppm (CON$\underline{H}$, D, J = 9 Hz) - |
| | 2 H at 7.40 ppm (N$\underline{H_2}$ of thiazole, Se.) - |
| | 1 H at 6.90 ppm (H of thiazole, S) - |
| | 1 H at 5.95 ppm (H$_7$, D of D, J$_1$ = 4 Hz, J$_2$ = 9 Hz) - |
| SR 41383 A | 1 H at 5.0 ppm (H$_6$, D, J = 4 Hz) - |
| | 2 H at 4.20 ppm (C$\underline{H_2}$—S—C(=N)N, AB, $J_{AB}$ = 13 Hz - |

-continued

| Code number | NMR spectrum |
|---|---|
| | 2 H at 3.80 ppm (C$\underline{H_2}$SO, AB, $J_{AB}$ = 17 Hz) - |
| | 3 H at 2.95 ppm (C$\underline{H_3}$N, S) - |
| | 3 H at 2.80 ppm (C$\underline{H_3}$N, S) - |
| | 6 H at 1.45 ppm ((C$\underline{H_3}$)$_2$C, S) |
| SR 41384 A | 1 H at 9.40 ppm (N$\underline{H}$, Se) - |
| | 1 H at 8.50 ppm (CON$\underline{H}$, D, J = 9 Hz) - |
| | 2 H at 7.40 ppm (N$\underline{H_2}$ of thiazole, Se.) - |
| | 1 H at 6.90 ppm (H of thiazole, S) - |
| | 1 H at 5.96 ppm (H$_7$, D of D, J$_1$ = 9 Hz, J$_2$ = 4 Hz) - |
| | 1 H at 5.00 ppm (H$_6$, D, J = 4 Hz) - |
| | 2 H at 4.00 ppm (C$\underline{H_2}$—S—C(=N)N, AB, $J_{AB}$ = 13 Hz) - |
| | 2 H at 3.80 ppm (C$\underline{H_2}$—SO—, AB, $J_{AB}$ = 17 Hz) - |
| | 6 H at 3.25 ppm ((C$\underline{H_3}$)$_2$N, Se.) - |
| | 3 H at 3.05 ppm (C$\underline{H_3}$NH, Se.) - |
| | 6 H at 1.45 ppm ((C$\underline{H_3}$)$_2$C, S). |
| SR 41385 A | 1 H at 9.20 ppm (N$\underline{H}$ C$_2$H$_5$, Se.) - |
| | 1 H at 8.50 ppm (CON$\underline{H}$, D, J = 9 Hz) - |
| | 2 H at 7.50 ppm (N$\underline{H_2}$ of thiazole, Se.) - |
| | 1 H at 6.80 ppm ($\underline{H}$ of thiazole, S) - |
| | 1 H at 5.96 ppm (H$_7$, D of D, J$_1$ = 9 Hz, J$_2$ = 4 Hz) - |
| | 1 H at 5.00 ppm (H$_6$, D, J = 4Hz) - |
| | 2 H at 4.10 ppm (C$\underline{H_2}$—S—C(=N)N, AB, $J_{AB}$ = 13 Hz) - |
| | 2 H at 3.8 ppm (C$\underline{H_2}$—SO, AB, $J_{AB}$ = 17 Hz) |
| | 6 H at 3.50 ppm (C$\underline{H_2}$N, M) - |
| | 6 H at 1.45 ppm ((C$\underline{H_3}$)$_2$C, S) |
| | 9 H at 1.20 ppm (C$\underline{H_3}$CH$_2$N, M) |
| SR 41605 A | 1 H at 9.25 ppm (= $^+$N$\underline{H}^-$, SE) |
| | 1 H at 8.50 ppm (—N$\underline{H}$—CO, D, J = 9 Hz |
| | 1 H at 6.80 ppm (H thiazole, S) |
| | 1 H at 5.95 ppm (H$_7$, D of D, J$_1$ = 9 Hz, J$_2$ = 4 Hz) |
| | 1 H at 5.0 ppm (H$_6$, D, J = 4 Hz) |
| | 1 H at 4.10 ppm (C$\underline{H_2}$S—C(=N)N, D, J = 13 Hz |
| | 1 H at 3.95 ppm (C$\underline{H_2}$—S—C(=N)N, D, J = 13 Hz) |
| | 1 H at 3.90 ppm (—C$\underline{H_2}$S(→O)—, D, J = 17 Hz) |
| | 1 H at 3.75 ppm (C$\underline{H_2}$S(→O)—, D, J = 17 Hz) |

| Code number | NMR spectrum |
|---|---|
| | 2 H at 3.50 ppm (CH$_3$—CH$_2$—N—, M) |
| | 6 H at 3.20 ppm (—N(CH$_3$)(CH$_3$), Se.) |
| | 6 H at 1.45 ppm (—C(CH$_3$)(CH$_3$)—, S) |
| | 3 H at 1.12 ppm (—N—CH$_2$—C$\underline{H_3}$, T, J = 7 Hz) |
| SR 41609 A | 1 H at 9.10 ppm (N$\underline{H}$—CH$_3$, Se.) |
| | 1 H at 8.45 ppm (N$\underline{H}$—CO, D, J = 9 Hz) |
| | 1 H at 6.75 ppm (H thiazole, S) |
| | 1 H at 6.0 ppm (H$_7$, D of D, J$_1$ = 9 Hz, J$_2$ = 4 Hz) |
| | 1 H at 5.0 ppm (H$_6$, D, J = 4 Hz) |
| | 1 H at 4.15 ppm 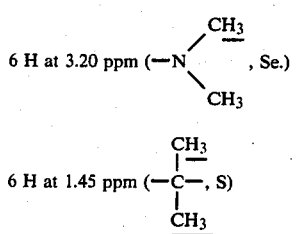 (C$\underline{H_2}$S—C(N)(N), D, J = 13 Hz) |
| | 2 H at 3.95 ppm (C$\underline{H_2}$S—C(N→O)(N) and C$\underline{H_2}$S—, M) |
| | 1 H at 3.80 ppm (C$\underline{H_2}$S, D, J = 17 Hz |
| | 4 H at 3.40 ppm 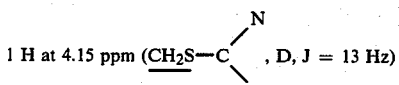 (—N(CH$_2$)(CH$_2$), M) |
| | 3 H at 3.05 ppm (NH—C$\underline{H_3}$, Se.) |
| | 4 H at 1.90 ppm 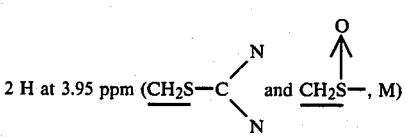 (—N(CH$_2$)(CH$_2$)(CH$_2$), M) |
| | 6 H at 1.45 ppm 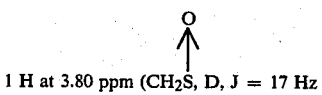 (—C(CH$_3$)(CH$_3$), Se.) |
| SR 91912 A | 1 H at 6.90 ppm (H thiazole, S) |
| | 1 H at 5.95 ppm (H$_7$, M) |
| | 1 H at 5.0 ppm (H$_6$, M) |
| | 6 H at 3.15 ppm 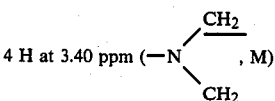 (—N(CH$_3$)(CH$_3$); Se.) |
| | 3 H at 3.05 ppm (NH—C$\underline{H_3}$, D, J = 7 Hz) |
| | 4 H at 2.40 ppm 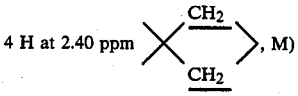 M) |
| | 2 H at 1.90 ppm  (C$\underline{H_2}$, M) |

The products of the invention can therefore be used as antibiotics in human and veterinary medicine. They can be used in all sensitive-bacterial infections.

The products of the invention have been analyzed concerning their pharmacological properties, and, in particular, their bacteriostatic action.

The in vitro bacteriostatic action was determined in a solid medium by the dilution method.

The results expressed in minimum inhibiting concentrations (MIC in μg/ml) are the results obtained on different strains.

These results are summarized in Table 2.

TABLE 2

| product | Escherichia coli R 69/3 Tem | Proteus 1510 | Klebsiella RO 30 | Enterobacter P 99 |
|---|---|---|---|---|
| CM 41 089 | 0.25 | ≦0.125 | 0.5 | 1 |
| SR 41 361 A | 0.5 | 0.5 | 0.5 | 1 |
| SR 41 362 A | 0.25 | ≦0.125 | 0.5 | 2 |
| SR 41 363 A | 0.5 | 4 | 2 | 16 |
| SR 41 380 A | 0.25 | ≦0.125 | 0.5 | 1 |
| SR 41 381 A | ≦0.125 | ≦0.125 | 0.5 | 1 |
| SR 41 382 A | 0.25 | ≦0.125 | 0.5 | 1 |
| SR 41 383 A | 0.5 | 1 | 2 | 8 |
| SR 41 384 A | 0.25 | ≦0.125 | 0.5 | 1 |
| SR 41 385 A | ≦0.125 | ≦0.125 | 0.5 | 2 |
| SR 41 605 A | 0.25 | ≦0.125 | 0.5 | 0.5 |
| SR 41 609 A | ≦0.125 | ≦0.125 | 0.5 | 0.5 |
| SR 41 912 A | ≦0.125 | ≦0.125 | 0.5 | 2 |

The tests conducted on animals failed to reveal any toxicity of the products according to the invention.

The pharmaceutical compositions are prepared from compounds (1) in their acidic form, or, if their solubility is insufficient, in the form of a salt.

The pharmaceutical compositions may be solid or liquid, and may be made up, for example, in the form of tablets, capsules, granules, ointments, creams, gels or preparations for injection.

The posology may vary within broad proportions, especially according to the type and gravity of the infection to be treated, and according to the method of administration. As a rule, in the adult and by injection, it ranges between 0.250 and 4 g daily.

As an example of a pharmaceutical composition, one may prepare ampules containing:
CM 41 089: 1 g
L-Lysin: 0.212 g
water for injection: 4 ml

We claim:

1. Cephalosporin compounds having the formula:

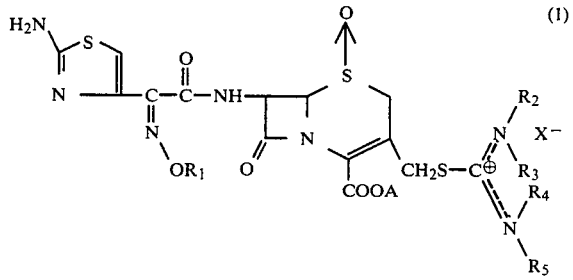

in the form of syn or anti isomers or a mixture of these isomers, and in which the acidic group —COOA is selected from the class consisting of pharmaceutically acceptable acids, salts, and easily hydrolysable esters;

R₁ represents a group:

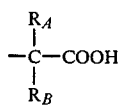

in which $R_A$ and $R_B$ each independently designates hydrogen or a lower alkyl group, or $R_A$ and $R_B$, taken together with the carbon atom to which they are bonded, form a cycloalkyl;

$R_2$ and $R_3$ each independently designates hydrogen, a lower alkyl group, a lower alkenyl group; or $R_4$ and $R_5$, taken together with the nitrogen atom to which they are bonded, form a ring selected from the class consisting of

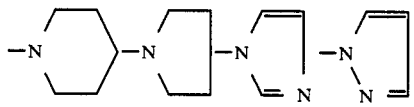

and X designates the anion of an acid.

2. Cephalosphorin compounds of claim 1, wherein both $R_A$ and $R_B$ are methyl groups.

3. Cephalosporin compounds of claim 1, wherein $R_A$ and $R_B$, taken together with the carbon atom to which they are bonded, form a cyclobutyl group.

4. A pharmaceutical composition for the treatment of bacterial infections comprising a therapeutically effective amount of a compound having the formula (1) of claim 1, in association with a pharmaceutically acceptable carrier.

5. A cephalosporin compound of claim 1, wherein R₁ is —C(CH₃)₂COOH; $R_2 = R_3 = R_4 = R_5 = CH_3$; and $X = CF_3COO^{31}$, said compound being the trifluoroacetate of the 1-S-oxide of 7-[2-(2-aminothiazol-4-yl)-2-(2-carboxy-2-propyloxyimino)acetamido]-3-[N,N,N′,N′-tetramethyluroniumthiomethyl)-3-cephem-4-carboxylic acid.

6. A cephalosporin compound of claim 2, wherein R₁ is —C(CH₃)₂COOH; $R_2 = R_3 = CH_3$; and

is the group of formula

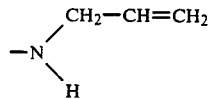

7. A cephalosporin compound of claim 1, wherein R₁ is —C(CH₃)₂COOH; $R_2 = R_3 = CH_3$; and

is the group of formula

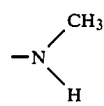

8. A cephalosporin compound of claim 1, wherein R₁ is —C(CH₃)₂COOH; $R_2 = R_3 = CH_3$; and

is the group of the formula —NH—C₂H₅.

* * * * *

UNITED STATES PATENT AND TRADEMARK OFFICE
CERTIFICATE OF CORRECTION

PATENT NO. : 4,578,377
DATED : March 25, 1986
INVENTOR(S) : LABEEUW et al.

It is certified that error appears in the above-identified patent and that said Letters Patent is hereby corrected as shown below:

For claim 1 of the patent, read:

--1. Cephalosporin compounds having the formula:

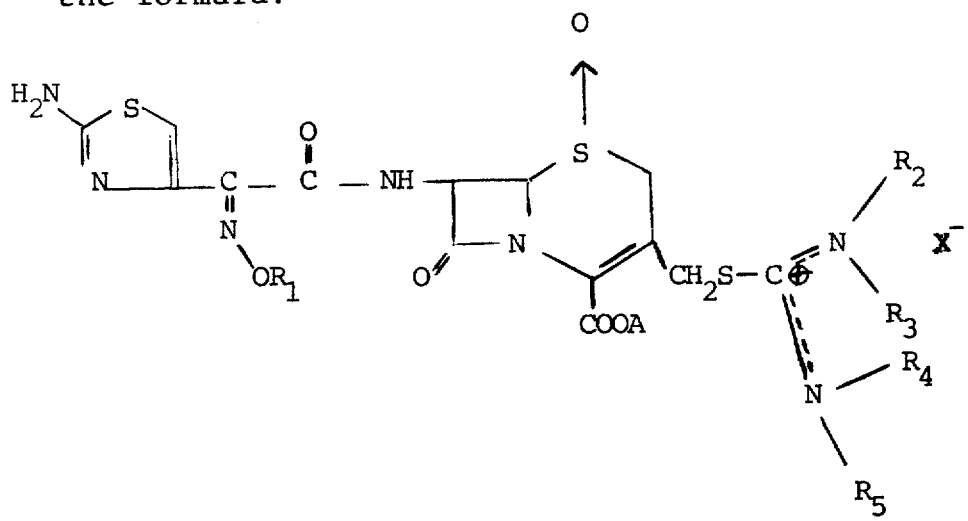

in the form of syn or anti isomers or a mixture of these isomers, and in which the acidic group -COOA is selected from the class consisting of pharmaceutically acceptable acids, salts, and easily hydrolysable esters;

UNITED STATES PATENT AND TRADEMARK OFFICE
CERTIFICATE OF CORRECTION

PATENT NO. : 4,578,377
DATED : March 25, 1986
INVENTOR(S) : LABEEUW et al.

It is certified that error appears in the above-identified patent and that said Letters Patent is hereby corrected as shown below:

$R_1$ represents a group;

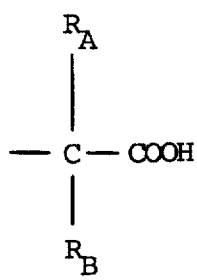

in which $R_A$ and $R_B$ each independently designates hydrogen or a lower alkyl group, or $R_A$ and $R_B$, taken together with the carbon atom to which they are bonded, form a cycloalkyl;

UNITED STATES PATENT AND TRADEMARK OFFICE
CERTIFICATE OF CORRECTION

PATENT NO. : 4,578,377
DATED : March 25, 1986
INVENTOR(S) : LABEEUW et al.

It is certified that error appears in the above-identified patent and that said Letters Patent is hereby corrected as shown below:

$R_2$ and $R_3$ each independently designates hydrogen, a lower alkyl group, a lower alkenyl group; $R_4$ and $R_5$ each independently designates hydrogen, a lower alkyl group, a lower alkenyl group, or $R_4$ and $R_5$, taken together with the nitrogen atom to which they are bonded, form a ring selected from the class consisting of

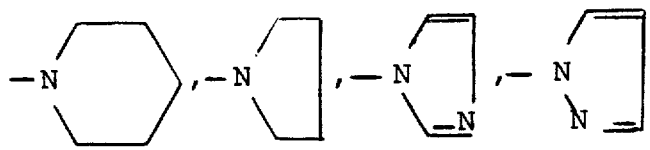

and X designates the anion of an acid

Signed and Sealed this

Ninth Day of September 1986

[SEAL]

Attest:

DONALD J. QUIGG

Attesting Officer  Commissioner of Patents and Trademarks